US008790287B2

(12) United States Patent
Evans

(10) Patent No.: US 8,790,287 B2
(45) Date of Patent: Jul. 29, 2014

(54) ORTHOPEDIC PADDING

(75) Inventor: John C. Evans, Lancashire (GB)

(73) Assignee: BSN Medical, Inc., Charlotte, NC (US)

( * ) Notice: Subject to any disclaimer, the term of this patent is extended or adjusted under 35 U.S.C. 154(b) by 41 days.

(21) Appl. No.: 13/464,284

(22) Filed: May 4, 2012

(65) Prior Publication Data

US 2012/0220908 A1   Aug. 30, 2012

Related U.S. Application Data

(63) Continuation of application No. 11/863,880, filed on Sep. 28, 2007, now abandoned.

(60) Provisional application No. 60/827,534, filed on Sep. 29, 2006.

(51) Int. Cl.
*A61F 13/00* (2006.01)
*D04B 21/00* (2006.01)
*A61F 13/04* (2006.01)
*D04B 21/16* (2006.01)

(52) U.S. Cl.
CPC ......... *A61F 13/041* (2013.01); *D10B 2403/021* (2013.01); *D10B 2509/02* (2013.01); *D10B 2509/028* (2013.01); *D04B 21/16* (2013.01)
USPC ................... 602/60; 602/62; 602/63; 602/75; 602/76; 442/304; 66/169 R

(58) Field of Classification Search
USPC .......... 602/60–63, 75, 76; 442/304, 306, 308, 442/311, 312, 318; 66/169 R, 170, 171, 66/178 A, 192, 193, 195
See application file for complete search history.

(56) References Cited

U.S. PATENT DOCUMENTS

| 5,256,134 A * | 10/1993 | Ingham ............................ 602/8 |
| 5,380,260 A * | 1/1995 | Blott ................................ 602/41 |
| 5,651,847 A * | 7/1997 | Loeffler ............................ 66/19 |
| 5,749,843 A * | 5/1998 | Miller ............................. 602/75 |
| 6,116,059 A * | 9/2000 | Rock et al. ...................... 66/191 |
| 6,711,920 B2 * | 3/2004 | Akers et al. ..................... 66/170 |
| 6,981,955 B2 * | 1/2006 | Schultze et al. ................. 602/3 |
| 2003/0114782 A1 * | 6/2003 | Chiang et al. .................... 602/6 |
| 2006/0155226 A1 * | 7/2006 | Grim et al. ....................... 602/6 |

* cited by examiner

*Primary Examiner* — Particia Bianco
*Assistant Examiner* — Keri J Nelson
(74) *Attorney, Agent, or Firm* — Shumaker, Loop & Kendrick, LLP

(57) ABSTRACT

An orthopedic padding including an elongate spacer fabric having spaced faces interconnected and separated by an intermediate spacer area, the spaced faces having a knitted construction different from a knitted construction of the intermediate spacer area, and the elongate fabric constructed at least in part of hydrophobic monofilament yarn knitted in an open construction for breathability.

15 Claims, 8 Drawing Sheets

ORTHOPEDIC PADDING

CROSS-REFERENCE TO RELATED APPLICATIONS

This continuation application claims priority to U.S. application Ser. No. 11/863,880 filed Sep. 28, 2007, which claims priority to U.S. Provisional Application No. 60/827,534 filed Sep. 29, 2006, the contents of each of which are incorporated by reference herein.

BACKGROUND OF THE INVENTION

This invention relates to an orthopedic padding, for example for use as an undercast liner of the type used to protect and cushion the skin of a patient from the relatively rigid material of a cast, such as those constructed of plaster of Paris or synthetic cast tape. The liner allows the patient to carry out routine activities such as bathing, showering, swimming, and the like without fear of the liner getting wet.

Traditional cast padding is constructed from a simple stockinette and padding material made from cotton or synthetic fibers, and offers poor or no water resistant capability. Cotton and some synthetic paddings actually absorb and retain large quantities of water. A cast is typically worn for a period of 6-8 weeks. During this period of time, traditional casts having a water-absorbent stockinette can promote skin maceration, discomfort. Traditional cast paddings can also breed odor causing bacteria as perspiration and water from washing and bathing migrates to and through the stockinette. The stockinette remains wet or damp for an extended period of time, causing the problems mentioned above.

The present invention provides a more conformable, water-resistant liner at a reduced cost as compared to water resistant products already available in the market. The present invention is directed to a construction that overcomes the drawbacks of water-resistant undercast liners such as that found in U.S. Pat. Nos. 5,102,711 and 5,277,954. For example, the monofilament structure of the liner has higher elongation in the width direction and provides a higher stretch during application that results in a better conforming liner which can be easily molded around a limb. Due to the improved padding/cushioning as compared to other liner and padding products known in the prior art, the undercast liner of the present invention requires fewer layers during application. The present invention may also have an adhesive coating incorporated on either or both surfaces. The tacky surface, when applied away from the skin, adheres to itself sufficiently to form a smoother underlayer for a cast. Additionally, it provides a non-slip effect under the cast tape and keeps the liner in position to facilitate easier application of the cast tape.

One of the problems with conventional cast padding as well as commercially available water resistant padding is that the padding collapses underneath a cast over the duration of 4-6 weeks as water and perspiration are absorbed into the structure. This reduction in thickness and resultant increase in density retards moisture transfer by both wicking and evaporation, and lessens the protection offered by the padding.

A water-resistant undercast liner such as disclosed and claimed in this application can help alleviate skin maceration problems which generally require additional treatment or therapy and eliminates the need for frequent cast changes. The present invention accommodates bathing, showering and contact with water without significant penetration of water into the padding, therefore keeping the skin relatively dry. In addition, the padding of the present invention provides improved conformability, cushioning, breathability, ease of application and a low profile as compared to a traditional undercast liner.

One embodiment of the invention uses a knitted spacer fabric having highly resilient monofilament yarns that allow the padding to keep its shape and loft when applied under an orthopedic cast. This feature also ensures less layers are needed than typical paddings used in this field. The materials and structure of the present invention offer excellent drainage and drying properties due to low surface area and low surface energy. The present invention can be used with an adhesive applied to one side, away from the skin, that permits a more effective non-slip effect, however, the knitted spacer material can be used with no adhesive layer.

The present invention is a very cost effective method of avoiding skin maceration problems arising from wearing an orthopedic cast over a period of weeks. The present invention will avoid the need for frequent cast changes arising for getting the orthopedic cast and padding wet. The present invention affords the opportunity to shower and bath and keep the skin clean with water without damaging the padding and also allows removal of the orthopedic cast using a cast saw without fear of cutting through the padding so improving comfort and safety.

BRIEF SUMMARY OF THE INVENTION

Therefore, it is an object of the invention to provide an orthopedic padding, for example a water resistant undercast liner.

It is another object of the invention to provide an orthopedic padding that is comfortable when worn under a plaster or synthetic cast.

It is another object of the invention to provide an orthopedic padding that is relatively thin and thus provides a low profile undercast liner layer when properly overlapped during application.

It is another object of the invention to provide an orthopedic padding that is relatively open and therefore breathable.

It is another object of the invention to provide an orthopedic padding that is resistant to collapse during extended use.

It is another object of the invention to provide an orthopedic padding that promotes drainage of water from the cast/liner if wetting does occur.

It is another object of the invention to provide an orthopedic padding that is highly resilient.

It is another object of the invention to provide a breathable undercast orthopedic padding.

It is another object of the invention to provide a breathable orthopedic undercast padding that is comfortable when worn against the skin under a plaster or synthetic cast, brace, splint or other orthopedic device.

It is another object of the invention to provide an orthopedic padding that is breathable and easy to clean.

It is another object of the invention to provide a breathable orthopedic padding that is resilient, low profile and protects honey prominences when fitted under a cast or splint.

These and other objects of the present invention are achieved by providing a breathable orthopedic undercast-padding product that comprises a knitted spacer fabric using monofilament yarns in an open construction.

According to one preferred embodiment of the invention, the knitted spacer fabric has between 4 and 20 courses per inch.

According to yet another preferred embodiment of the invention the wales per inch are between 6 and 28 per inch.

According to yet another preferred embodiment of the invention the spacer fabric is constructed using 4 to 6 bars.

According to yet another preferred embodiment of the invention the construction of the spacer fabric uses monofilament yarns.

According to yet another preferred embodiment of the invention the Monofilament yarns are Nylon, Polyester or Polypropylene materials.

According to yet another preferred embodiment of the invention a Multifilament yarn could be incorporated into the structure.

According to yet another preferred embodiment the multifilament yarns are between 0.03 and 1.2 mm in diameter.

According to yet another object of the invention a multifilament yarn could be used with a decitex range of 33 to 156.

According to yet another embodiment of the invention the multifilament yarn could be Nylon, Polyester, Polypropylene, or any synthetic fiber.

According to yet another preferred embodiment of the invention the multifilament yarns would be knitted on the surface of the padding.

According to yet another embodiment of the invention the knitted structure should be between 1 mm and 10 mm in thickness.

According to yet another preferred embodiment of the invention the weight of the padding material should be between 40 and 160 gsm.

According to yet another preferred embodiment of the invention the padding material should have a lengthways stretch of between 0 (zero) and 100 percent.

According to yet another preferred embodiment of the invention the surface of the padding is coated with an adhesive.

According to yet another preferred embodiment of the invention the adhesive is applied at a coating level of 3 to 50 gsm by weight.

According to yet another preferred embodiment of the invention the padding could be used with no adhesive layer.

In accordance with one embodiment of the invention, an orthopedic padding for being applied to an anatomical shape of a patient and overlaid with a cast material is provided, and comprises an elongate fabric having two opposing faces and an intermediate spacer area that both separates and interconnects the opposed faces. The padding is constructed at least in part of hydrophobic, water resistant monofilament yarn for providing enhanced water resistance, light weight, breathability and resistance to collapse and degradation due to moisture and bacteria during extended use of the padding. The padding has sufficient stretch in both a length-wise and width-wise direction to facilitate conforming the padding around the anatomical shape without wrinkling during application.

According to another embodiment of the invention, the yarn is selected from the group consisting of polypropylene, polyester, polyethylene, and nylon.

According to another embodiment of the invention, the padding is formed by one or more fabric-forming techniques selected from the group consisting of weaving, knitting, nonwoven, and stitching.

According to another embodiment of the invention, the fabric is treated with at least one finish for providing additional water resistance, anti-bacterial, anti-odor, or aromatherapy characteristics to improve the functionality of the padding or enhance the cast-wearing experience for the patient.

According to another embodiment of the invention, the padding includes an adhesive coating on at least one of the inner and outer faces to aid in application to the patient by adhering to itself and thus maintaining placement of partially overlying layers relative to each other as the padding is applied.

According to another embodiment of the invention, the padding has higher elongation in the width direction than in the length direction for allowing greater stretch during application.

According to another embodiment of the invention, the adhesive is preferably a low tack, pressure sensitive adhesive selected from the group consisting of acrylic and silicone adhesive.

According to another embodiment of the invention, the monofilament yarn has a diameter of at least 0.03 mm.

According to another embodiment of the invention, the monofilament yarn has a diameter of between approximately 0.05 and approximately 0.25 mm.

According to another embodiment of the invention, an orthopedic padding is provided, wherein the padding is constructed using a pillar and inlay stitch on the inner and outer faces and a needle V in the spacer area, and the yarn has a diameter of approximately 0.03 to approximately 0.25 mm. The padding is formed with at least 50 courses per meter and weighs between approximately 50 to approximately 400 grams per square meter.

According to another embodiment of the invention, the padding weighs between approximately 100 to approximately 250 grams per square meter and has a nominal thickness when not compressed or under tension of approximately 1.5 to approximately 3.5 mm.

According to another embodiment of the invention, the padding includes a fluorochemical, silicone or other water repellant finish to improve drainage and provide faster drying.

According to another embodiment of the invention, an orthdpedic padding for being applied to an anatomical shape of a patient and overlaid with a cast material is provided, and comprises a tubular fabric having two opposing faces and an intermediate spacer area that both separates and interconnects the opposed faces. The padding is constructed at least in part of hydrophobic, water resistant monofilament yarn for providing enhanced water resistance, light weight, breathability and resistance to collapse and degradation due to moisture and bacteria during extended use of the padding. The padding has sufficient stretch in both a length-wise and width-wise direction to facilitate conforming the upadding around the anatomical shape during application.

According to another embodiment of the invention, the padding includes a water repellant finish to improve drainage and provide faster drying.

According to another embodiment of the invention, an orthopedic pading for being applied to an anatomical shape of a patient and overlaid with a cast material is provided, and comprises an elongate fabric in roll form having two opposing faces and an intermediate spacer area that both separates and interconnects the opposed faces. The padding is constructed at least in part of hydrophobic, water resistant monofilament yarn for providing enhanced water resistance, light weight, breathability and resistance to collapse and degradation due to moisture and bacteria during extended use of the padding. The padding has sufficient stretch in both a length-wise and width-wise direction to facilitate conforming the padding around the anatomical shape during application.

According to another embodiment of the invention, the monofilament yarn has a diameter of between approximately 0.05 and approximately 0.25 mm.

According to another embodiment of the invention, the padding is constructed using a pillar and inlay stitch on the inner and outer faces and a needle V in the spacer area. The yarn has a diameter of approximately 0.03 to approximately 0.25 mm, and the liner is formed with at least 50 courses per meter and weighs between approximately 50 to approximately 400 grams per square meter.

According to another embodiment of the invention, the padding weighs between approximately 100 to approximately 250 grams per square meter and has a nominal thickness when not compressed or under tension of approximately 1.5 to approximately 3.5 mm.

BRIEF DESCRIPTION OF THE DRAWINGS

Some of the objects of the invention have been set forth above. Other objects and advantages of the invention will appear as the invention proceeds when taken in conjunction with the following drawings, in which.

DETAILED DESCRIPTION OF THE INVENTION

Figure 1:
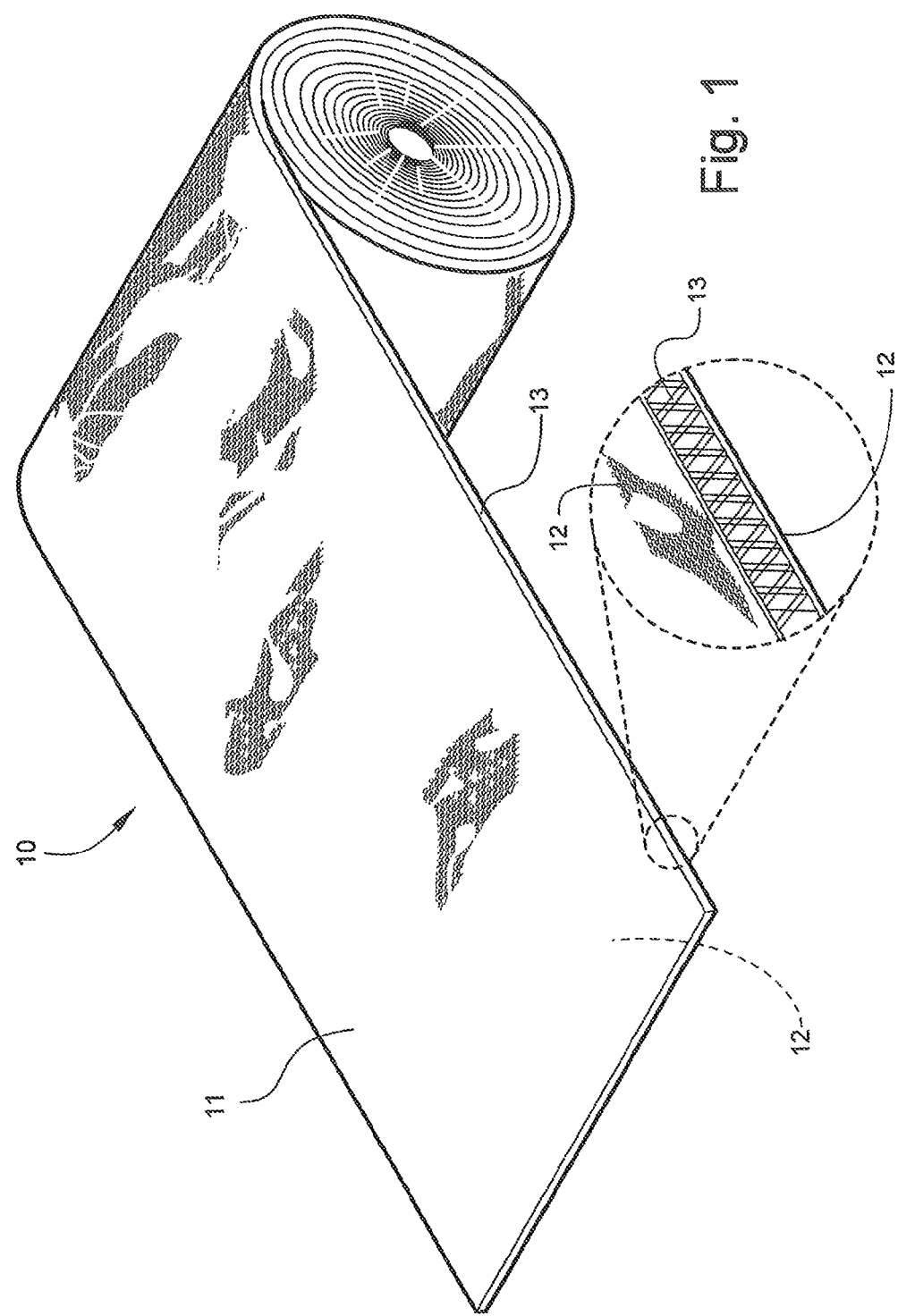
FIG. 1 is a perspective view of a roll of an orthopedic padding according to one embodiment of the invention.
Figure 2:
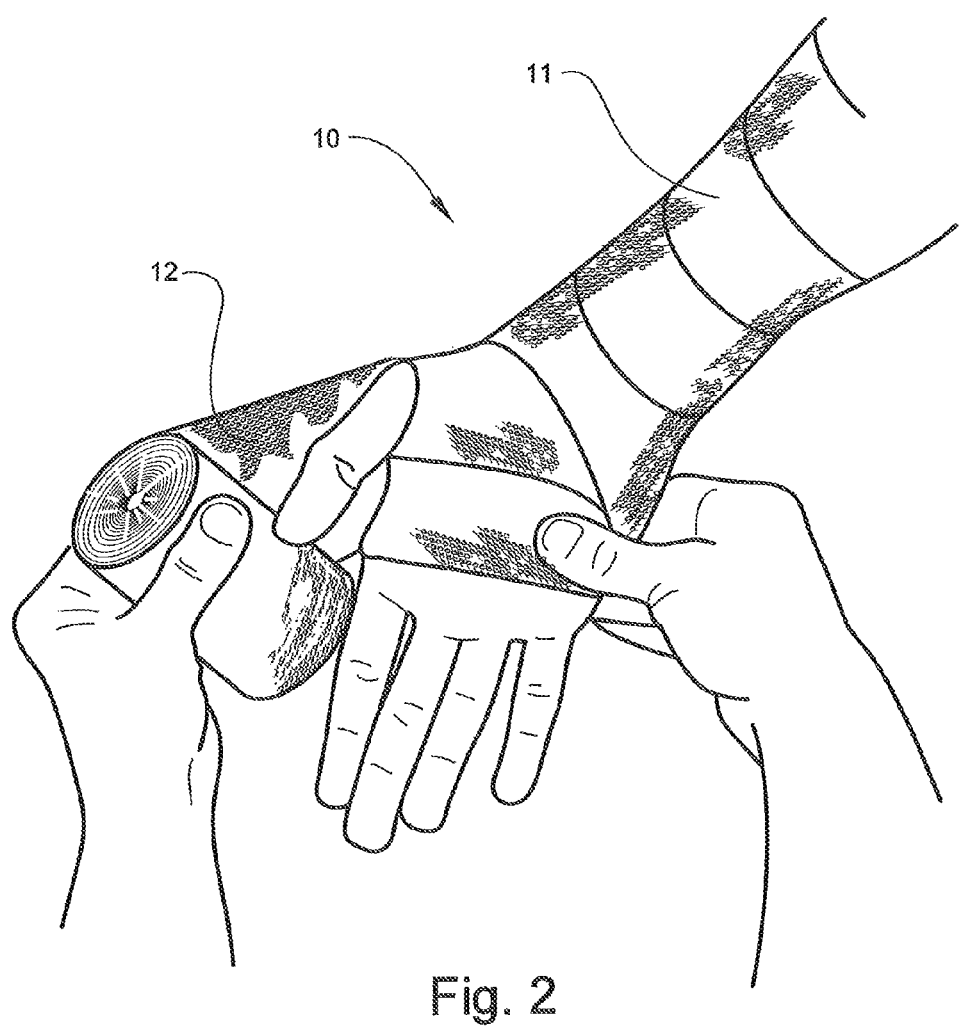
FIG. 2 is a view illustrating application of the orthopedic padding to the wrist and forearm.
Figure 3:
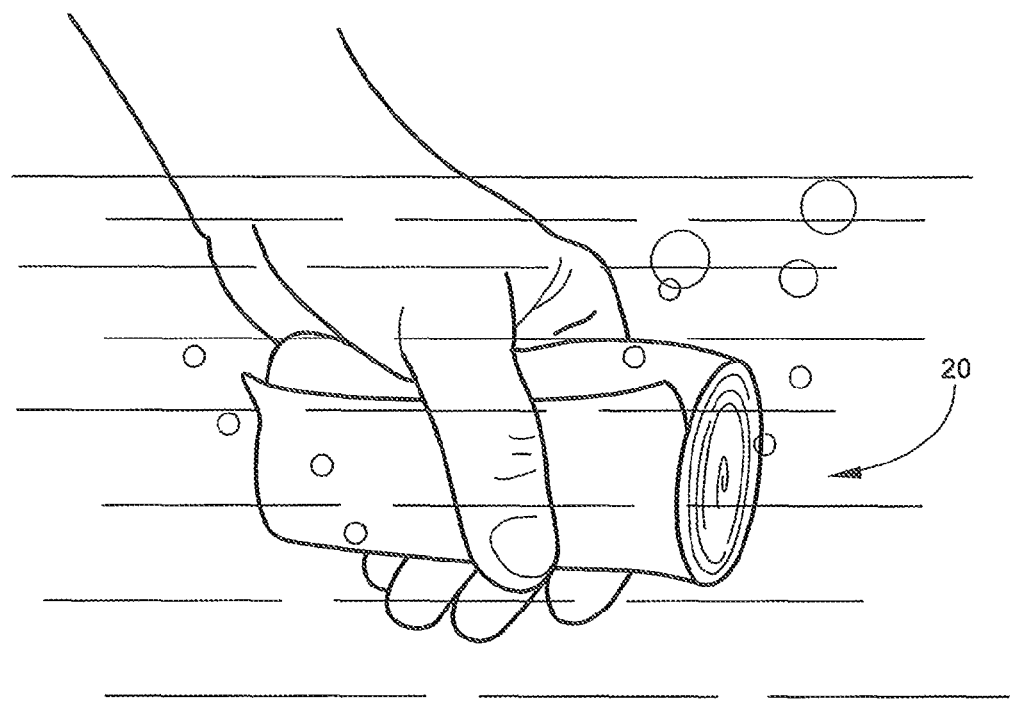
FIGS. 3 and 4 illustrate preparation of a cast tape for application over the orthopedic padding.

Referring now specifically to the drawings, an orthopedic padding, for example for use as an undercast liner according to the present invention is illustrated in FIG. 1 and shown generally at reference numeral 10. While the undercast liner 10 can be formed in any desired width or length, the undercast liner 10 shown in FIGS. 1, 2, and 3 is about 7.5 cm (about 3 in.) wide and is formed into a roll during manufacture for shipping and storage until use. The undercast liner 10 is easily applied from the roll, as shown in FIG. 2. The liner 10 includes two opposing faces 11, 12 and an intermediate spacer area 13 that both separate and interconnect the faces 11, 12, as described in further detail below. The undercast liner 10 can be formed in a tubular form or in an elongate padding form in a roll.

The liner 10 can be constructed using any suitable organic or inorganic monofilament yarn, preferably a hydrophobic/water resistant monofilament yarn such as polypropylene, polyester, polyethylene and nylon. The monofilament yarn used for constructing the liner 10 preferably has a diameter of at least 0.03 mm. The liner 10 is constructed in a spacer fabric construction to provide sufficient cushioning and breathability, and it has been found that the use of a monofilament hydrophobic yarn on both faces 11, 12 and in the spacer area 13 provides enhanced water resistance, light weight, breathability and resistance to collapse and degradation due to moisture and bacteria during extended use.

The liner 10 is formed using any suitable fabric forming technology such as weaving, various knitting techniques such as, for example, weft knitting and warp knitting, non-woven, stitching, or a combination of these techniques. Preferably, the structure should provide some stretch in both the lengthwise and width-wise directions, and facilitate conforming the undercast liner 10 around an anatomical shape during application.

The liner 10 can be treated with one or more finishes to provide additional water resistance, anti-bacterial and/or anti-odor characteristics, or aromatherapy to improve the functionality or enhance the cast-wearing experience for the patient. Alternatively, the liner 10 can be fabricated from modified/treated monofilament yarns incorporating suitable fillers or finishes to improve the performance of the liner 10.

The liner 10 may also be provided with an adhesive coating on one or both faces 11, 12 to aid in application to the patient. The adhesive is preferably any suitable low tack, pressure sensitive adhesive, such as an acrylic or silicone adhesive. The adhesive aids in application by adhering to itself and thus maintaining the exact placement of the layers relative to each other as the liner 10 is applied by the cast technician.

In one preferred embodiment, the liner 10 is constructed as a spacer fabric using polypropylene monofilament and a low tack, pressure sensitive adhesive on one surface. The monofilament yarn has a diameter of at least 0.03 mm, and preferably between 0.05-0.25 mm. Preferably, the liner 10 requires no additional finish or water repellency treatment.

More specifically, the preferred embodiment of the liner 10 is constructed of a polypropylene monofilament yarn on a double needle bed knitting machine, and can be knitted on either a warp knitting Raschel machine or a Crochet knitting machine. The liner 10 is preferably constructed using a pillar and inlay stitch on the surfaces 11, 12 and a 3 or 5 needle V in the spacer area 13. The yarn has a diameter of 0.03-0.25 mm. The fabric for the liner 10 is formed with at least 50 courses per meter preferably 200-850 courses per meter. The liner 50 weighs between 50-400 grams per square meter, and more preferably between 100-250 grams per square meter. The liner 10 has a nominal thickness when not compressed or under tension of approximately 1.5-3.5 mm.

Alternatively, an undercast liner may be constructed as a spacer fabric with at least one of the yarns being a multifilament or spun yarn in order to provide even more patient comfort. The liner may be treated with suitable fluorochemical, silicone or other water repellant finish to improve drainage and provide faster drying.

Referring now to FIG. 2, the undercast liner 10 is applied to the injured limb in a conventional manner. As noted above, the stretch provided by the undercast liner 10 permits a fast, accurate, closely-conforming application without wrinkles or creases.

Figure 4:
Figure 5:
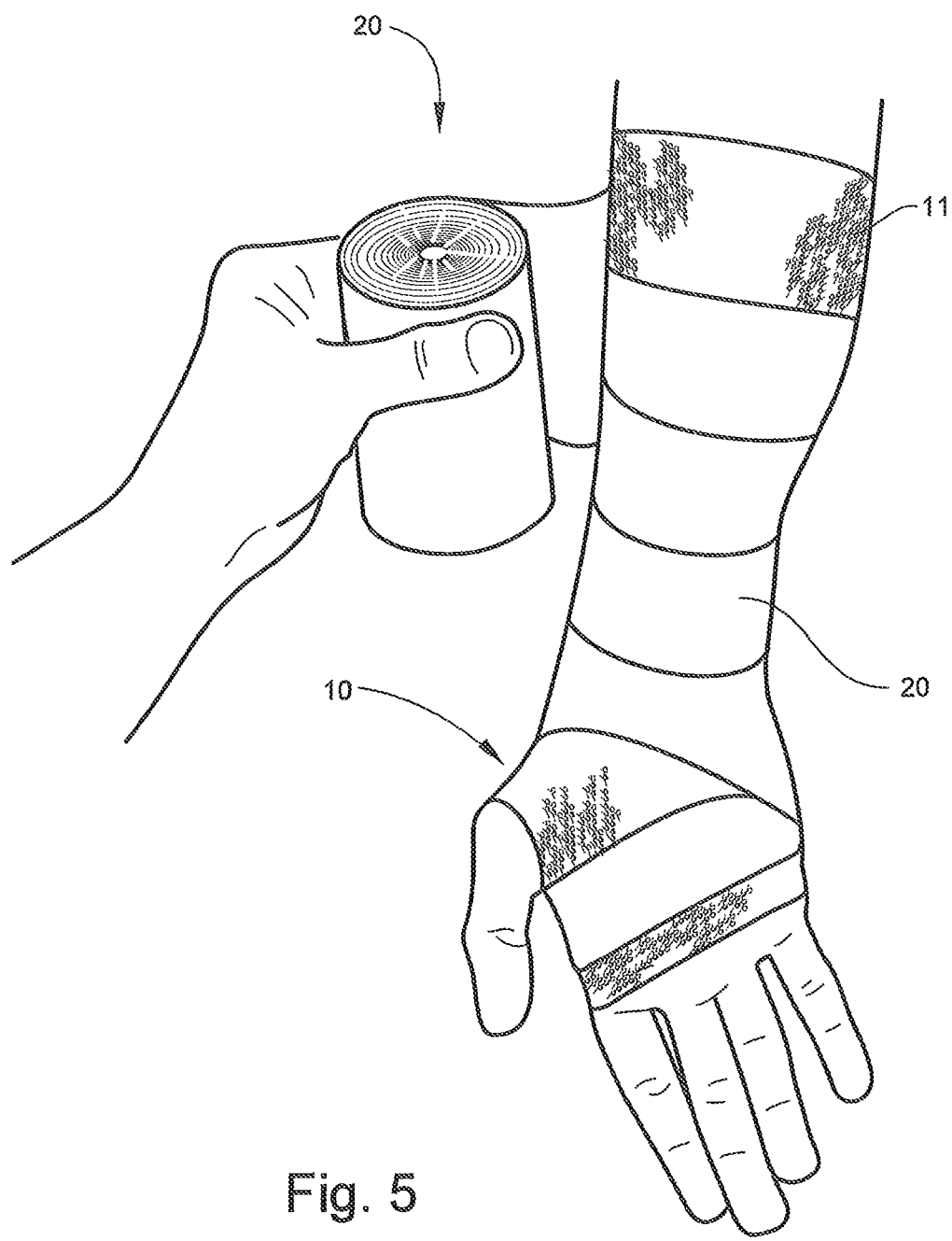
FIGS. 5 and 6 illustrate application of the cast tape to the orthopedic padding.
Figure 6:
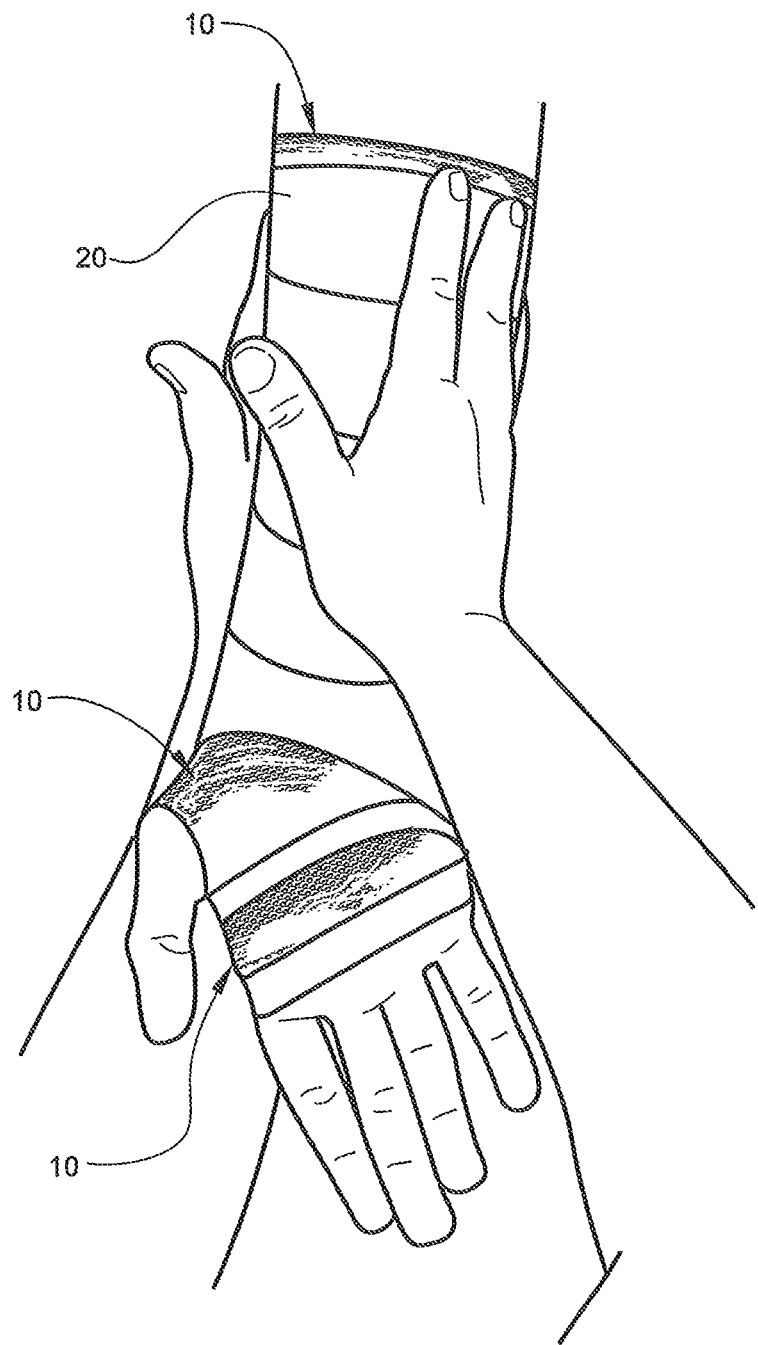
Figure 7:
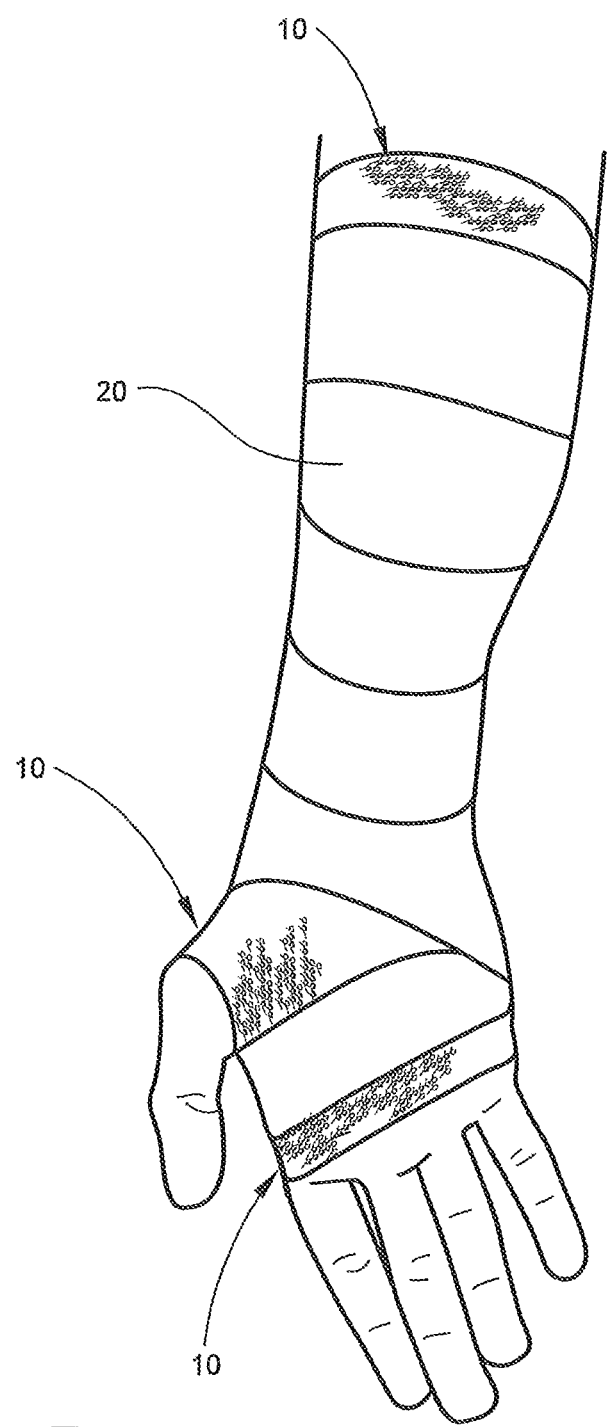
FIG. 7 illustrates the completed cast.

As is shown in FIGS. 3-7, after application of the undercast liner 10, a conventional cast tape 20 is wetted, FIG. 3, excess water removed by wringing, FIG. 4, and applied to the injured limb, FIGS. 5-7, taking care in the usual manner to avoid overlapping the undercast liner 10 on opposite ends, leaving a short width of exposed undercast liner 10.

Figure 8:
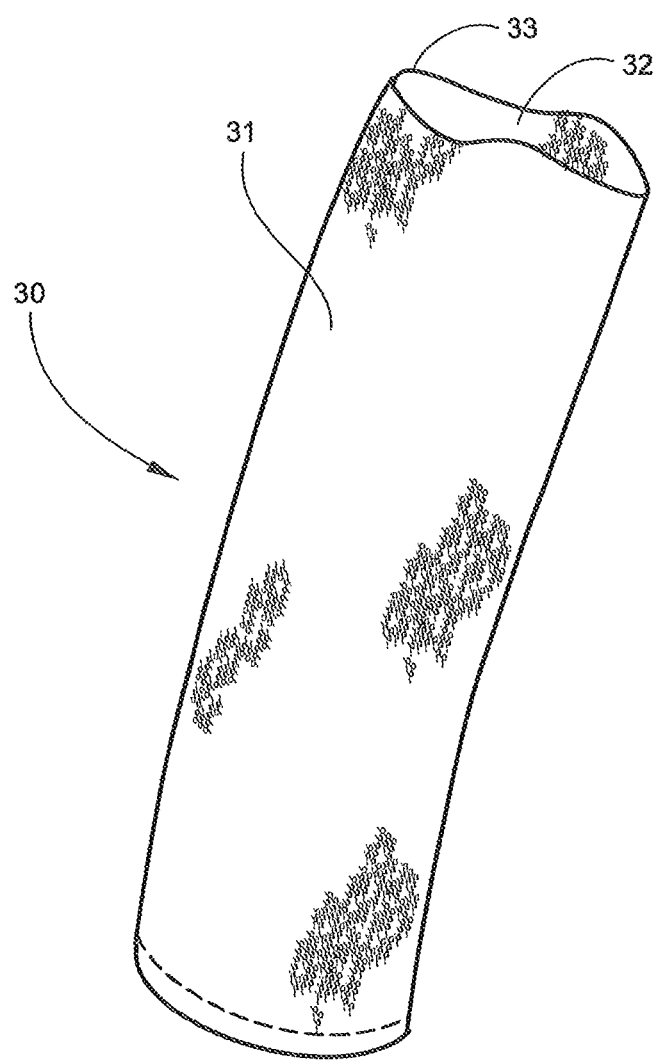
FIG. 8 illustrates a liner in the form of a circular sleeve.
Figure 9:
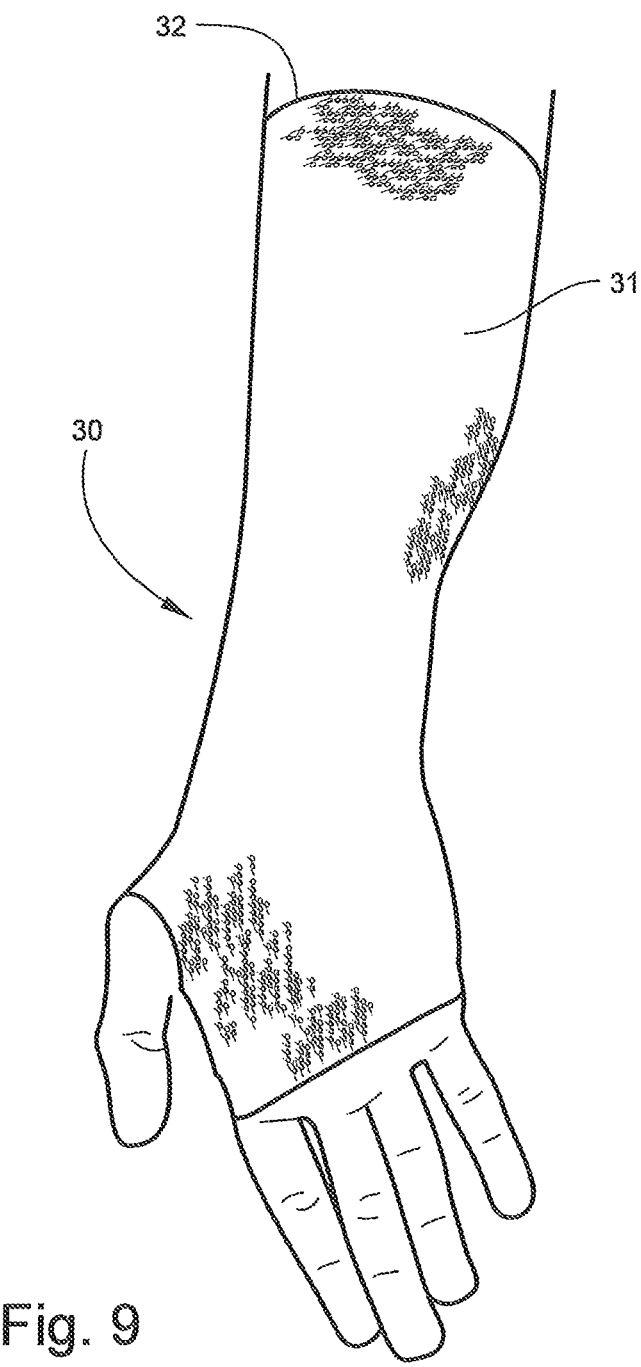
FIG. 9 shows the sleeve in place on an arm prior to application of a cast tape bandage.

Referring now to FIG. 8, a circular knit liner 30 is shown, preferably with the same preferred constructions described above. The liner 30 includes an outer face 31, an inner face 32 and a spacer area 33 that both separates and interconnects the two faces 31, 32, as shown in FIG. 1. Instead of wrapping, the liner 30 is pulled onto the limb as shown in FIG. 9, in the same manner as a conventional stockinette. Thereafter, a cast tape 20 is applied in a conventional manner.

A further embodiment includes a knitted spacer fabric constructed from monofilament yarns. The monofilament yarns may be of the type selected from Nylon, Polypropylene or Polyester yarns or a mixture thereof.

The monofilament yarns may be between 0.03 mm and 1.5 mm in diameter.

The substrate may have a thickness of between 0.5 and 10 mm.

The substrate weight may be between 40 and 160 grams per square meter.

The substrate may have between 4 and 20 courses per inch.

The substrate is between 6 and 28 wales per inch.

The substrate may contain a multifilament yarn.

The substrate may be used in a bandaging product or in a compression bandage, and may incorporate elastic yarns.

An orthopedic padding for example for use as an undercast liner is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

What is claimed is:

1. An orthopedic padding, comprising:
   a knitted elongate spacer fabric defining a first and second opposing faces each having a pillar inlay stitch construction interconnected and separated from one another through an intermediate spacer area having a needle V stitch construction such that the first and second opposing faces and the intermediate spacer area are knitted together but differ in knit construction, all of the first and second opposing faces and the spacer area constructed from hydrophobic monofilament yarn, and
   the knitted elongate spacer fabric constructed of hydrophobic monofilament yarn knitted in an open construction for breathability, wherein:
   the orthopedic padding is an undercast liner,
   the knitted elongate spacer fabric has a higher elongation in its width direction than in its length direction,
   the hydrophobic monofilament yarn is selected from the group consisting of nylon and polyethylene,
   at least one of the spaced faces being configured to directly contact a user's skin;
   the orthopedic padding comprising multifilament yarn knitted on a surface of at least one of the spaced faces for comfort; and
   the multifilament yarn ranging between 0.03 mm and 1.2 mm in diameter.

2. The orthopedic padding according to claim 1, wherein the multifilament yarn has a decitex range from 33 to 156.

3. The orthopedic padding according to claim 1, wherein the spacer fabric comprises between 4 and 20 courses per inch.

4. The orthopedic padding according to claim 1, wherein the spacer fabric comprises between 6 and 28 wales per inch.

5. The orthopedic padding according to claim 1, wherein the spacer fabric is constructed using 4 to 6 bars.

6. The orthopedic padding according to claim 1, wherein the hydrophobic monofilament yarn is polyethylene.

7. The orthopedic padding according to claim 1, wherein the orthopedic padding has an overall thickness between 1 mm and 10 mm.

8. The orthopedic padding according to claim 1, wherein the spacer fabric has a weight between 40 gsm and 160 gsm.

9. The orthopedic padding according to claim 1, wherein each spaced face is coated with an adhesive applied at a coating level of 3 to 50 gsm by weight, the adhesive is a silicone adhesive.

10. The orthopedic padding according to claim 1, wherein the monofilament yarn has a diameter between 0.05 mm and 0.25 mm.

11. The orthopedic padding according to claim 1, wherein the orthopedic padding has an overall thickness when not compressed or under tension of 1.5 mm to 3.5 mm.

12. The orthopedic padding according to claim 1, wherein the spacer fabric is treated with silicone.

13. The orthopedic padding according to claim 1, wherein the spacer fabric is knitted in the form of a tube.

14. An orthopedic padding consisting of:
    a knitted elongate spacer fabric defining a first and second opposing faces each having a pillar inlay stitch construction interconnected and separated from one another through an intermediate spacer area having a needle V stitch construction such that the first and second opposing faces and the intermediate spacer area are knitted together but differ in knit construction, all of the first and second opposing faces and the spacer area constructed from hydrophobic monofilament yarn, and
    at least one of the spaced faces being coated with an adhesive applied at a coating level of 3 to 50 gsm by weight;
    the spacer fabric being treated with a fluorochemical, and
    the knitted elongate spacer fabric constructed of hydrophobic monofilament yarn knitted in an open construction for breathability, wherein:
    the orthopedic padding is an undercast liner,
    the knitted elongate spacer fabric has a higher elongation in its width direction than in its length direction,
    the hydrophobic monofilament yarn is selected from the group consisting of nylon and polyethylene, the hydrophobic monofilament yarn has a diameter between 0.05 mm and 0.25 mm,
    at least one of the spaced faces being configured to directly contact a user's skin;
    the orthopedic padding comprising multifilament yarn knitted on a surface of at least one of the spaced faces for comfort; and
    the multifilament yarn ranging between 0.03 mm and 1.2 mm in diameter.

15. The orthopedic padding according to claim 14, wherein the orthopedic padding has an overall thickness between 1 mm and 10 mm.

* * * * *